United States Patent
Kvist et al.

(10) Patent No.: US 7,858,139 B2
(45) Date of Patent: Dec. 28, 2010

(54) EMULGATING AGENT FROM CEREAL GRAINS

(75) Inventors: Sten Kvist, Odakra (SE); John Mark Lawther, Gevninge (DK)

(73) Assignee: Biovelop AB, Kimstad (SE)

( * ) Notice: Subject to any disclaimer, the term of this patent is extended or adjusted under 35 U.S.C. 154(b) by 1034 days.

(21) Appl. No.: 11/608,992

(22) Filed: Dec. 11, 2006

(65) Prior Publication Data

US 2007/0128331 A1 Jun. 7, 2007

Related U.S. Application Data

(63) Continuation of application No. PCT/SE2005/000961, filed on Jun. 17, 2005.

(30) Foreign Application Priority Data

Jun. 17, 2004 (SE) .................................. 0401566

(51) Int. Cl.
A23D 7/00 (2006.01)
(52) U.S. Cl. ....................... 426/602; 426/601
(58) Field of Classification Search ................. 426/602
See application file for complete search history.

(56) References Cited

U.S. PATENT DOCUMENTS

| 5,686,123 | A | * | 11/1997 | Lindahl et al. ................. 426/28 |
|---|---|---|---|---|
| 5,814,341 | A | | 9/1998 | Fankhauser et al. |
| 6,284,886 | B1 | * | 9/2001 | Redmond ..................... 536/124 |
| 6,323,338 | B1 | * | 11/2001 | Potter et al. ............. 536/123.12 |
| 7,105,195 | B2 | * | 9/2006 | Plank et al. .................. 426/601 |
| 7,138,519 | B2 | * | 11/2006 | Morgan .................. 536/123.12 |
| 2002/0016454 | A1 | * | 2/2002 | Potter et al. ............. 536/123.12 |
| 2004/0049026 | A1 | * | 3/2004 | Potter et al. ............. 536/123.12 |
| 2005/0089602 | A1 | * | 4/2005 | Kvist et al. .................... 426/52 |

FOREIGN PATENT DOCUMENTS

EP 1361264 11/2003
WO 98/34501 8/1998

OTHER PUBLICATIONS

Terelli, F. 1997. Journal of Food Science 62(6)1194.*
Kontogiorgos, V. 2004. Food Hydrocolloids 18:987.*
Temelli et al., "Extraction and functional properties of barley B-Glucan as affected by temperature and PH" Journal of Food Science, vol. 62, No. 6, 1997, pp. 1194-1197.
Burkus et al., "Stabalization of emulsions and foams using barley B-glucan" Food Research International, vol. 33, 2000, pp. 27-33.
Database WPI, Week 200357, Derwent Publications Ltd., London, GB, AN 2003-601473, & JP 2003081999, Mar. 19, 2003.
Database WPI, Week 199703, Derwent Publications Ltd., London, GB, AN 1997-029424 & JP 3555907 B2, Apr. 18, 2004.

* cited by examiner

*Primary Examiner*—Carolyn A Paden
(74) *Attorney, Agent, or Firm*—Gauthier & Connors LLP

(57) ABSTRACT

The present invention relates to a process for preparing a stable emulsion/dispersion of an oil and an aqueous phase, wherein a β-glucans rich substrate, derived from oat or barley grain, is the active emulsifying component.

35 Claims, No Drawings

EMULGATING AGENT FROM CEREAL GRAINS

PRIORITY INFORMATION

This application is a continuation of International Application Serial No. PCT/SE2005/000961 filed on Jun. 17, 2005 which claims priority to Swedish Application No. 0401566-5 filed Jun. 17, 2004, both of which are incorporated herein by reference in their entirety.

TECHNICAL FIELD

The present invention relates to a process for preparing stable emulsions, or non-separating mixtures, of oils and other non-water miscible liquids, with water or predominantly aqueous solutions and suspensions, wherein emulsification and stabilization is engendered by an oat or barley derived β-glucans rich material. The emulsions are used as the basis for a number of foodstuffs, such as full-fat and reduced fat mayonnaises, dressings, dips and spreads, as well as for cosmetic formulations wherein natural emulsions are required.

BACKGROUND OF THE INVENTION

There are manifold areas in the food industry wherein stabilized mixtures and emulsions of oil and water rich phases are produced and utilized. Specific products are mayonnaises, dressings, dips, and spreads of the margarine, edible oil/fat and butter based types. Many fat rich sauces also possess emulsion characteristics.

For many of these products, emulsification and emulsion stability is achieved using well-known emulsifiers which are of surfactants. Among the most utilized are lecithin and a number of mono- and di-glycerides. Mono glycerides are particularly useful for the production of low fat, high water spreads. GB 574,389 is one of the original patents in this field.

There is a growing interest and consumer demand for healthier products with reduced fat contents, particularly in the range of products mentioned above. There are acknowledged methods for the preparation of reduced fat foodstuffs comprising emulsions and a number of patented methodologies exist. Examples are: EP 0 420 315, EP 0 422 712, U.S. Pat. No. 4,849,243 which focus on reduced- and low-fat spreads.

Much recent interest has focused on the incorporation of soluble fiber type polysaccharides and oligosaccharides such as inulin to improve water-binding, lower overall fat within, and thicken the aqueous component of, emulsified products such as dressings and spreads. A process for low-fat emulsified dressings containing inulin is described in EP 0 792 587. However, egg yolk which is rich in lecithin is used as the emulsifier, and high shear emulsification is used to produce the final dressing. Soluble fibers such as inulin are also acknowledged pre-biotic materials and are considered to promote good gut-health in humans, and their incorporation in foodstuffs is therefore also interesting from a health standpoint. However, as mentioned above, it is necessary in many such products to add one of the standard emulsifiers, or indeed to incorporate at least a chemically modified starch, which performs a similar function and is no longer a natural product.

Starch is also widely used as a fat-replacement in products such as low-fat mayonnaises, and in spreads, for example U.S. Pat. No. 4,591,507, however the addition of a standard emulsifier is almost always necessary unless the starch is chemically modified (JP 2000-236810). It is therefore recognized that it would be beneficial to utilize a natural product that can emulsify, stabilize products such as dressings, mayonnaises and spreads, particularly if a beneficial soluble fiber component can be incorporated into the final product, and especially if reduced fat and low fat food products can be produced in a simple, reliable manner. To date, however, this has proved difficult and very few natural ingredients and processes allow the easy manufacture of such products.

EP-A-1 361 264 discloses a fat or oil compositions containing gramineous β-glucans, which are produced at an elevated temperature using preferably β-glucans having a lower molecular weight, i.e., a molecular weight below 500,000, often below 200,000, more often below 100,000 Dalton. Emulsions made from such β-glucans have to be violently agitated using high-shear mixing apparatuses in order to obtain a stable emulsion. Using non-high shear mixing will lead to a phase separation of the emulsion.

The present invention addresses many of these issues. We have discovered a natural emulsifying agent which produces stable emulsions of edible oils, fats and other non-water-miscible liquids in water. Moreover, the emulsion is produced without resource to high energy or high shear mixing using this emulsifier. This emulsifying agent can be used to produce emulsions to be used in foodstuffs such as reduced fat mayonnaises, dressings, dips, full-fat and reduced fat spreads, sauces and also for the production of emulsified cosmetic products for atopic application. In this invention, materials obtained from oat or barley grains which are rich in healthy (1-3),(1-4)-β-D-glucans are utilized in a specific way to enable the formation of stable emulsions and dispersions.

SUMMARY OF THE PRESENT INVENTION

The invention aims to:
1. Produce stable emulsions/dispersions of oils and aqueous phases, in which β-glucans rich substrate, derived from oat or barley grain (which may consist of the isolated bran fraction), is the active emulsifying and stabilizing component
2. Attain a stable emulsion/dispersion in a step-wise sequence: add the β-glucans rich powder or granulate to the oil phase or to a part of the oil phase and mix and disperse, followed by addition of the aqueous phase with concomitant mixing and stirring. The water phase is preferably, but not essentially, warmed to about 30° C. prior to addition, but is normally kept at room or ambient temperature, i.e., around 20 to 22° C. However, stable emulsions will be formed at even lower temperatures, if so needed or suitable.
3. Attain emulsions/dispersions that are suitable as bases for a number of foodstuffs, such as full and reduced fat mayonnaises, dressings, dips etc, reduced fat spreads based on mixtures of butters, other edible fats and water or any suitable combination of fats, oils and water, reduced and normal fat sauces, reduced fat ingredients for baked and other products to replace or partially replace the fat conventionally used in the products.
4. Produce finished products in the categories listed above using the invented process. Alternatively, cosmetic products for topic application can be prepared using the same invented method.

It has to our surprise been discovered that substrates of oat and/or barley grains or bran, which contain at least 12% β-glucans, preferably at least 13% by weight, more preferably at least 14%, still more preferably 15% by weight of β-glucans on a dry weight basis, of a demonstrable average molecular weight of at least 1 million Daltons, can emulsify and stabilize mixtures of non-water miscible liquids such as oils, and water, or predominantly aqueous solutions and suspensions, as emulsions or dispersions provided a stepwise procedure is followed and that the β-glucans rich preparation is added at a level of between 2% and 10%, optionally up to 25%, of the final mixture formulation. The stepwise procedure is as follows:

A. The required amount β-glucans rich material, preferably in a dry powder or granulate form, is added to the oil phase, or a portion of the oil phase, with stirring, mixing or other suitable agitation, such as a kitchen mixer at lowest speed, or even a spoon being performed until the particulate substrate is dispersed in the medium and each particle is wetted by the oil. The mixture can optionally be warmed to 30° C. or higher, but below 40° C. to facilitate improved dispersion. Further oil can be added at this stage if required.

B. The water or predominantly aqueous component is then added with concomitant stirring, mixing or other suitable method of agitation, but not using a high shear or high energy mixer or mixing system, and the β-glucans component of the mixture swells, rapidly taking up the added water and concomitantly bringing the two phases together into a stable emulsion/dispersion mixture. It is beneficial, but not essential to warm the aqueous component to 30° C. or higher prior to addition and mixing and to perform the mixing at the temperature used.

C. The mixture, if warmed, is allowed to cool or is actively cooled, preferably, but not necessarily, whilst stirring is continued.

In the case of a margarine type spread, this final phase can of course be a continuous cold-scraping procedure familiar to those skilled in the art of making full-fat and fat-reduced spreads.

The oil phase can be any edible vegetable oil or vegetable fat in the melted state, or any animal fat or fat rich material such as butter or butterfat in the melted state where foodstuffs are the desired final product. Examples of such oils and fats are: Olive oil in Extra Virgin, Virgin and cold-pressed forms, Rapeseed oil which is prepared conventionally or cold-pressed, sunflower oil, soy oil, maize oil, cotton-seed oil, peanut oil, sesame oil, shea nut fats, cereal germ oil such as wheat germ oil, grape kernel oil, palm oil and palm kernel oil, linseed oil, coconut fats, butter and butter fats, hardened vegetable oils, fish oils, or any blends and combinations of these materials. This list is illustrative only and the invention of course can utilize all oils and fats coming from renewable sources and their mixtures. In cases where the end product is a cosmetic product, i.e. an emulsion or dispersion for atopic application, established cosmetic and fragrance oils are included in the invention.

The β-glucans rich material can be of a type that is dry milled from oat or barley grain, with or without subsequent ethanol treatment, or can be a powder that has been wet-extracted from oat or barley grain or bran using alkali, or using enzyme treatment such as alpha amylase. The present invention is not concerned with the method of preparation of the β-glucans rich ingredient, only in it's utilization in the present context. The main criteria are that to stabilize emulsions and dispersions as described. The β-glucans component of the added ingredient should be at least 12% on a dry matter basis and that β-glucans should have an average molecular weight of at least 1 million Daltons.

Examples of Suitable Materials are:

Water or Alkaline extracts from either whole oat or barley grain, or from an enriched bran milled from the grains, which are subsequently neutralized and then dried to a powder, or alternatively precipitated into ethanol or an other organic solvent, or mixtures of ethanol or other organic solvent and water prior to drying. The latter precipitation step can further enrich the β-glucans content of the material.

Materials prepared from oat grain or bran via wet extraction wherein the β-glucans is solubilized after treatment by starch degrading enzymes such as alpha amylases. Wet milling can also be a component of the extraction regime. The extracts are subsequently dried to a powder or alternatively precipitated into ethanol or other organic solvent, or mixtures of ethanol or other organic solvent and water prior to drying. The latter precipitation step can further enrich the β-glucans content of the material.

Materials produced by combinations of the above two mentioned procedures.

Milled oat grain or bran, which has been heat treated prior to dehulling and milling, in which the β-glucans containing sub-aleurone and aleurone components of the grain has been enriched by physical means such as air classification, which may have also been further treated with ethanol or other such solvent to reduce fat and sugar content, thereby further enriching the β-glucans content. These materials also contain most of the insoluble bran type fiber from the grain.

This list should not be regarded as exhaustive as any preparation from oat or barley grain and/or bran which contains 12% or more β-glucans on a dry matter basis, which component has an average molecular weight greater than 1 million Daltons, can be utilized in the invented process. It is understood by those skilled in the chemistry and processing of cereals that these particular β-glucans are correctly classified as (1-3),(1-4)-β-D-glucans and are found mainly in the sub-aleurone and aleurone layers of the oat and barley grains.

The β-glucans rich material is preferably utilized in a powder form, but can also be in the form of granulates or similar particulate solid state.

DETAILED DESCRIPTION OF THE PRESENT INVENTION

According to the present invention, a β-glucans rich material, derived from oat or barley grain or bran, is the active emulsifying and stabilizing ingredient producing stable dispersions and/or emulsions of oils and/or other non-water miscible liquids and water, or predominantly aqueous solutions and suspensions.

The present invention relates in particular to a process for preparing a stable emulsion/dispersion of an oil and an aqueous phase wherein a β-glucans rich powder or granulate containing at least 12% by weight of β-glucans having a molecular weight of more than 1,000,000 Daltons is added in a step-wise sequence to the oil phase or to a part of the oil phase and is mixed and dispersed, followed by addition of the aqueous phase at temperatures below 40° C. with concomitant mixing and stirring to form an oil-in-water emulsion or a water-in-oil emulsion. The oil-water emulsion and/or dispersion is produced in a step-wise manner in which the first step is the mixing of the β-glucans rich component with the oil phase, in the absence of water, ensuring dispersion in, and surface-wetting of the β-glucans rich particles with, the oil phase. The aqueous phase is then subsequently added with stirring.

It is advantageous, but not essential, to warm the suspension of β-glucans rich material in oil and also to add the aqueous phase at a temperature of 30° C. or higher, but not above 40° C. This facilitates a rapid swelling of the β-glucans rich material and an effective emulsification and stabilization of the oil-water mixture.

An essential feature of the present invention is that mixing and stirring takes place using a low- or non-shear mixing, thus avoiding complex and energy consuming high-shear mixing processes and apparatuses, using no shearing forces.

The mixing in the first step, which is the incorporation of the β-glucans rich substrate into the oil phase, is readily accomplished using a standard mixer (for example a kitchen mixer or industrial mixer), stirrer, blender or any such suitable method of agitation. Upon addition of the aqueous phase, mixing is also achieved using a standard mixer (for example a kitchen mixer or industrial mixer), stirrer, blender or any such suitable method of agitation, which can include high sheer mixing of the type normally used to create oil in water and water in oil emulsions.

In a preferred embodiment, the emulsion/dispersion is attained using an active ingredient obtained from oat or barley grain or bran, which contains at least 10% β-glucans, preferably more than 12% β-glucans and which component has a demonstrable average molecular weight of at least 1 million Daltons. This ingredient is obtained preferably as a powder or granulates and is then firstly stirred into a non-water miscible liquid such as a fat or oil, into which it is dispersed, preferably but not essentially, with warming at a level of addition of between 1% and 10%, optionally up to 25%, on a weight basis, of the final product mass. The aqueous component is then added, preferably but not necessarily, at a temperature at or above 30° C., with stirring and a stable emulsion/dispersion is formed upon the swelling and thickening of the β-glucans component. The proportions of the oil component to the aqueous component within the product emulsion/dispersion ranges from 10% oil/90% aqueous component to 80% oil/20% aqueous component.

The molecular weight of the beta glucans present in the beta glucans ingredient is at least 1,000,000 Daltons, preferably at least 1,500,000 Daltons, more preferably 2,000,000 Daltons, still more preferably 3,000,000 Daltons.

The beta glucans ingredient normally comprising dextrins and other bran derivatives related to the preparation from oat and barley bran contains at least 12% by weight of β-glucans, preferably at least 13% by weight of β-glucans, more preferably at least 14% by weight of β-glucans, still more preferably at least 15% by weight of β-glucans, yet still more preferably at least 20% by weight of β-glucans and further still more preferably at least 25% by weight of β-glucans.

In a preferred embodiment, a powder or granulate derived from oat or barley grain or bran containing at least 12%, preferably more than 14%, β-glucans of required molecular weight is added to edible vegetable oil such as olive oil, rapeseed oil, maize oil, sunflower seed oil amongst many, at a level between 2% and 20% by weight and is incorporated into the oil by stirring, mixing or other suitable method of agitation. An aqueous material, which may be water or a solution containing other water-soluble ingredients, is then added, preferably but not necessarily, at a temperature at or above 30° C., to the oil rich mixture with stirring, mixing or other suitable method of agitation to a proportion ranging between 20% and 80%. At this stage other ingredients including egg, vinegar, salt, sugar, other flavorings, acidity regulators, texturants, stabilizers, preservatives, can optionally be added. A stable emulsion/dispersion is formed which is readily used as the basis for a number of food products such as full- and reduced fat mayonnaises, full- and reduced fat dressings and dips.

In a preferred embodiment, a powder or granulate derived from oat or barley grain or bran containing at least 12%, preferably more than 14% β-glucans of required molecular weight, is added to melted butter or butterfat, optionally containing up to 50% other vegetable oils such as cold-pressed or conventional rapeseed oil, cold-pressed or extra-virgin olive oil, amongst others, at a level between 2% and 20% by weight and is incorporated into the fat by stirring, mixing or other suitable method of agitation. An aqueous material, which may be water or a solution containing other water-soluble ingredients, is then added, preferably but not necessarily, at a temperature at or above 30° C., to the fat rich mixture with stirring, mixing or other suitable method of agitation to a proportion ranging between 20% and 80%. At this stage other ingredients including salt, other flavorings, colorants, acidity regulators, texturants, stabilizers, preservatives, can optionally be added. A stable emulsion/dispersion is formed which can be cooled with stirring to produce formulations for a range of reduced fat butter-based spreads, or as a reduced fat replacement, or partial replacement, of butter or butterfat in a number of baked products such as pastries, croissants, biscuits and cookies etc.

In a preferred embodiment, a powder or granulate derived from oat or barley grain or bran containing at least 12%, preferably more than 14% β-glucans of required molecular weight is added to melted, conventional fat (i.e. 75-85% fat content) margarine intended for cooking, baking or as a spread, at a level between 2% and 20% by weight and is incorporated into the liquid fat by stirring, mixing or other suitable method of agitation. An aqueous material, which may be water or a solution containing other water-soluble ingredients, is then added, preferably but not necessarily, at a temperature at or above 30° C., to the fat rich mixture with stirring, mixing or other suitable method of agitation to a proportion ranging between 20% and 80%. At this stage other ingredients including salt, other flavorings, colorants, acidity regulators, texturants, stabilizers, preservatives, can optionally be added. A stable emulsion/dispersion is formed which can be cooled with stirring to produce formulations for a range of reduced fat margarines for use as spreads, in cooking or as an ingredient for baking as a replacement or partial replacement of conventional fat or margarine in products such as pastries, cakes, croissants, breads, biscuits, cookies etc.

In a preferred embodiment, a powder or granulate derived from oat or barley grain or bran containing at least 12%, preferably more than 14%, β-glucans of required molecular weight is added to melted hard fat such as coconut fat or palm kernel oil, amongst others, i.e. those fats having melt indices of 20-25° C. and higher, optionally containing up to 50% other vegetable oils such as cold-pressed or conventional rapeseed oil, cold-pressed or extra-virgin olive oil, sunflower oil, amongst others, at a level between 2% and 20% by weight and is incorporated into the liquid fat by stirring, mixing or other suitable method of agitation. An aqueous material, which may be water or a solution containing other water-soluble ingredients, is then added, preferably but not necessarily, at a temperature at or above 30° C., to the fat rich mixture with stirring, mixing or other suitable method of agitation to a proportion ranging between 20% and 80%. At this stage other ingredients including salt, other flavorings, colorants, acidity regulators, texturants, stabilizers, preservatives, can optionally be added. A stable emulsion/dispersion is formed which can be cooled with stirring to produce formulations for a range of reduced fat spreads.

In a preferred embodiment, a powder or granulate derived from oat or barley grain or bran containing at least 12%, preferably more than 14%, β-glucans of required molecular weight is added to an edible vegetable oil such as olive oil, rapeseed oil, maize oil, sunflower seed oil amongst many, optionally containing up to 50% other vegetable oils such as cold-pressed or conventional rapeseed oil, cold-pressed or extra-virgin olive oil, amongst others, at a level between 2% and 20% by weight and is incorporated into the fat by stirring, mixing or other suitable method of agitation. An aqueous material, which may be water or a solution containing other water-soluble ingredients, is then added, preferably but not necessarily, at a temperature at or above 30° C., to the fat rich mixture with stirring, mixing or other suitable method of agitation to a proportion ranging between 20% and 80%. A stable emulsion/dispersion is formed which can be used as a reduced fat ingredient to replace completely or partially, the fat conventionally used in a number of baked products such as pastries, cakes, croissants, biscuits, muffins, breads etc.

In a preferred embodiment, a powder or granulate derived from oat or barley grain or bran containing at least 12%, preferably more than 14%, β-glucans of required molecular weight is added to an edible vegetable oil such as olive oil, rapeseed oil, maize oil, sunflower seed oil amongst many, or blends of such oils, which may optionally also include harder fats such as butter, butter-fats, coconut fat, at a level between 1% and 80% by weight and is incorporated into the oil by stirring, mixing or other suitable method of agitation, optionally with warming above 30° C. The suspended, wetted particles of the β-glucans rich material are then allowed to settle, and/or are actively centrifuged down, and the excess oil is decanted off manually or mechanically, or removed by filtration. The remaining oil wetted and coated material is then utilized as an ingredient to promote the rapid formation of emulsions and stable dispersions in food products ranging from low-fat mayonnaises, dressings, dips, spreads, sauces and as a basis to fat replacing formulations wherein water is bound into products via the β-glucans component.

In a preferred embodiment, a powder or granulate derived from oat or barley grain or bran containing at least 12%, preferably more than 14%, β-glucans of required molecular weight is added to an emollient or fragrance oil at a level between 1% and 20% by weight and is incorporated into the oil by stirring, mixing or other suitable method of agitation. An aqueous material, which may be water or a solution containing other water-soluble ingredients, is then added, preferably but not necessarily, at a temperature at or above 30° C., to the fat rich mixture with stirring, mixing or other suitable method of agitation to a proportion ranging between 20% and 80%. At this stage other ingredients including preservatives, other water-soluble cosmetic additives can be added. A stable emulsion/dispersion is formed which can be used in formulations for cosmetics for atopic application or directly as the cosmetic product. Applications include skin lotions and creams, sun-blockers and after-sun creams amongst others.

DESCRIPTION OF THE PREFERRED EMBODIMENTS

Example 1

Reduced Fat Mayonnaise

A β-glucans rich powder extracted from oat bran and comprising dextrins beside β-glucans and containing 28% β-glucans of average molecular weight at least 1.5 million Daltons, was added to 195 g of sunflower oil in a 1 liter glass beaker. 25 g of the powder was mixed with mechanical stirring using a standard kitchen mixer at low speed, into the oil until a smooth, clump free dispersion was obtained (approximately 30 seconds of mixing). The β-glucans containing substrate is become wetted by the oil. 195 g of water, warmed to 40° C., was added to the suspension with concomitant mixing using the same kitchen mixer. A rapid thickening and incorporation of the water into the oil mediated by the β-glucans component was observed. Mixing was continued for a further 4 minutes, during which time the other ingredients were added: 20 g of egg yolk, 10 g of whole egg, 7 g of sugar, 5 g of salt, and 13 g of vinegar. The mixture was allowed to cool to room temperature and was stirred for a further 1 minute.

A definite reduced fat (40% total fat as opposed to 80% for a conventional full fat product) mayonnaise product resulted, with good mouth feel, flavor and body. The β-glucans component in this product functions as an emulsifier/emulsion stabilizer, texturant and hydrocolloid.

Example 2

Healthy Dressing 20 g of the same β-glucans rich powder as used in example 1 (containing 28% β-glucans of average molecular weight greater than 1.5 million Daltons) was added to 100 g of sunflower oil, in a 1 liter glass beaker, with stirring using a standard kitchen mixer. When the blend was smooth and free of clumps (less than 2 minutes mixing time), 315 g of water warmed to 35° C. was added to the suspension with concomitant mixing using the same kitchen mixer. A rapid thickening and incorporation of the water into the oil mediated by the β-glucans component was observed. Mixing was continued for a further 4 minutes, during which time the other ingredients were added: 20 g of egg yolk, 10 g of whole egg, 7 g of sugar, 5 g of salt, 13 g of vinegar, and 8 g of milk protein isolate. The mixture was allowed to cool to room temperature and was stirred for a further 1 minute.

After cooling in a refrigerator, the product was in all ways (taste, mouth feel, texture, color etc) representative of a dip or high quality dressing. With a total fat content of 20%, the label reduced fat can be used comfortably with such a product.

Example 3

Reduced Fat Dip 2 g of the same β-glucans rich powder as used in Example 1 (containing 28% β-glucans of average molecular weight greater than 1.5 million Daltons) was added to 50 g of sunflower oil, in a 1 liter glass beaker, with stirring using a standard kitchen mixer. When the blend was smooth and free of clumps (less than 2 minutes mixing time), 365 g of water warmed to 35° C. was added to the suspension with concomitant mixing using the same kitchen mixer. A rapid thickening and incorporation of the water into the oil mediated by the β-glucans component was observed. Mixing was continued for a further 4 minutes, during which time the other ingredients were added: 20 g of egg yolk, 10 g of whole egg, 7 g of sugar, 5 g of salt, 13 g of vinegar, and 8 g of milk protein isolate. The mixture was allowed to cool to room temperature and was stirred for a further 1 minute.

After cooling in a refrigerator, the product was in all ways (taste, mouth feel, texture, color etc) representative of a dip or high quality dressing. With a total fat content of 10%, the label reduced fat can be used comfortably with such a product.

Example 4

Butter Based Spread 100 g of standard, low-salt, butter was placed in a 400 ml glass beaker and the butter was allowed to melt by placing the beaker in a water bath maintained at 40° C. When the butter had melted, 10 g of the same oat β-glucans rich preparation used in Examples 1 and 2 above was added, with mixing, to the liquid butter. After two minutes of further mixing, the suspension was smooth and free of any clumps and at this point 100 g of water, warmed to 35° C., was added to the mixture with fast stirring using a kitchen mixer. A further 1.5 g of salt was added during the stirring period (3 minutes). Within 2 minutes, the β-glucans component had thickened and concomitantly facilitated the incorporation of the melted butter into the water. The beaker was then transferred to an ice bath and stirring was continued using the same kitchen mixer until the mixture had reached a temperature of 5° C.

The product was found to taste very like the parent butter, spread easily from the refrigerator and had structure and mouth feel consistent with good quality spreads, with a fat content of just 40%.

Example 5

Reduced Fat Margarine 100 g of a standard, margarine was placed in a 400 ml glass beaker was allowed to melt by placing the beaker in a water bath maintained at 40° C. When the margarine had melted, 10 g of the same oat β-glucans rich preparation used in Examples 1 and 2 above was added, with mixing, to the liquid butter. After two minutes of further mixing, the suspension was smooth and free of any clumps and at this point 100 g of water, warmed to 35° C., was added to the mixture with fast stirring using a kitchen mixer. A further 1.5 g of salt was added during the stirring period (3 minutes). Within 2 minutes, the β-glucans component had thickened and concomitantly facilitated the incorporation of the melted margarine into the water. The beaker was then transferred to an ice bath and stirring was continued using the same kitchen mixer until the mixture had reached a temperature of 5° C.

The product was found to be very like the parent margarine, spread easily from the refrigerator and had structure and mouth feel consistent with good quality spreads, with a fat content of just 40%.

Example 6

Baking Margarine 120 g of a standard baking margarine was placed in a 400 ml glass beaker was allowed to melt by placing the beaker in a water bath maintained at 40° C. When the margarine had melted, 10 g of the same oat β-glucans rich preparation used in Examples 1 and 2 above was added, with mixing, to the liquid butter. After two minutes of further mixing, the suspension was smooth and free of any clumps and at this point 80 g of water, warmed to 35° C., was added to the mixture with fast stirring using a kitchen mixer. A further 1.5 g of salt was added during the stirring period (3 minutes). Within 2 minutes, the β-glucans component had thickened and concomitantly facilitated the incorporation of the melted margarine into the water. The beaker was then transferred to an ice bath and stirring was continued using the same kitchen mixer until the mixture had reached a temperature of 5° C.

The product was found to very like the parent margarine, spread easily from the refrigerator and had structure and mouth feel consistent with good quality spreads, with a fat content of just 50%. The product was utilized in two specific baking applications: a sweet "Danish" pastry recipe and a standard short-crust pastry for a flan or Quiche Lorraine. In both cases, the new mix was used in place of the normal margarine. Good products were obtained in both cases, with taste and mouth feel very similar to the normal full-fat pastries.

Example 7

Healthy Butter and Oil-Based Spread 75 g of standard, low salt, butter was placed in a 400 ml glass beaker and the butter was allowed to melt by placing the beaker in a water bath maintained at 40° C. When the butter had melted, 25 g of cold-pressed rapeseed oil was added along with 1 g of the same oat β-glucans rich preparation used in Examples 1 and 2 above, with mixing, to the liquid butter. After two minutes of further mixing, the suspension was smooth and free of any clumps and at this point 100 g of water, warmed to 35° C., was added to the mixture with fast stirring using a kitchen mixer. A further 1.5 g of salt was added during the stirring period (3 minutes). Within 2 minutes, the β-glucans component had thickened and concomitantly facilitated the incorporation of the melted buffer into the water. The beaker was then transferred to an ice bath and stirring was continued using the same kitchen mixer until the mixture had reached a temperature of 5° C.

The product was found to very like the parent butter, spread easily from the refrigerator and had structure and mouth feel consistent with good quality spreads, with a fat content of just 40%. The rapeseed oil component is cold-pressed and is particularly rich in mono-unsaturated and poly-unsaturated fatty acids, and is essentially free of trans-fatty acids. Extra Virgin or Extra Virgin cold-pressed olive oil can readily substitute the cold-pressed rapeseed oil in such a healthy spread formulation.

Example 8

Reduced Fat Oil for Baking Etc 10 g of the same oat β-glucans rich preparation used in examples 1 and 2 above was added, with mixing, to 95 g of rapeseed oil. The suspension was mixed until the powder component was evenly distributed in the oil (2 minutes mixing time). 95 g of water, warmed to 40° C., was then added with fast mixing to the suspension. A rapid thickening and incorporation of the water into the oil mediated by the β-glucans component was observed. The mixture was allowed to cool after a further 2 minutes of stirring and was found to be a stable dispersion/emulsion after 24 hours in the refrigerator.

The mixture containing 45% fat was then used in place of rapeseed oil in a number of baked products, including cakes (Swedish style "Sponge Cake" and muffins), biscuits and pastries. In a sugar, or sponge, cake, the mixture was used in place of the standard rapeseed oil. A cake of excellent quality and texture was produced with minor adjustments to the cake recipe. Equivalent satisfactory results were obtained in a muffin baking trial where the fat was replaced by the same mix.

The process of the present invention was compared to the one described in EP-A-1 361 264, which shows the use of low molecular weight β-glucans preparations to provide emulsions of fats and oils. Thus a number of tests were carried out using β-glucans preparations containing β-glucans having a molecular weight of 60,000 Daltons. As evident from the tests according to Comparative Examples 9-11 stable emulsion were obtained when using high-shear mixing only.

Comparative Example 9

100 g of Sunflower oil was placed in a 400 ml glass beaker. 12 g of a β-glucans rich powder extracted from oat grain, containing 45% β-glucans of average molecular weight of 60,000 Daltons, was added to the oil with stirring until a smooth, clump-free dispersion was obtained. 100 g of warm (35° C.) water was added to the mixture with concomitant stirring using a kitchen mixer on a low-setting, for 5 min. A suspension was obtained, with no significant thickening and this suspension rapidly separated (within 3 minutes) on standing at room temperature.

The same mixture was then high shear mixed using a Silverson L4R mixer fitted with an emulsor screen for high sheer mixing, for 3 minutes. A thin, but stable emulsion resulted. No thickening effect was observed in this case.

Comparative Example 10

The same procedure as reported in example 9 was performed, except that the 12 g of powder containing 45% β-glucans of average molecular weight 60,000 Daltons, was mixed into 100 g of the sunflower oil at a temperature of 80° C. and the dispersion was held at this temperature for 2 hours prior to the addition of the water as described in example 9.

No differences in behaviour as compared to those observed in example 9, were noted, and high sheer mixing was required to create an emulsion, as above.

Comparative Example 11

A milled oat bran product containing 9.2% β-glucans (analysis using the McCleary Method, AACC standard method 32-23, for mixed linkage β-glucans), milled to a particle size of less than 250 microns, was used. 13 g of the powder was added to 100 g of sunflower oil and stirred with a low speed kitchen mixer to aid dispersion for 5 minutes. 100 g of lukewarm water (35° C.) was then added with continued low-speed stirring for a further 5 min. No notable thickening of the mix was observed and after standing for a further 3 minutes, the mixture had separated into an oil phase, a water phase and much of the powder had settled at the bottom of the beaker.

The same mixture was then high shear mixed using a Silverson L4R mixer fitted with an emulsor screen for high sheer mixing, for 3 minutes. An unstable dispersion resulted, which showed immediate signs of separation and the aqueous and oil phases were largely separated after 1 hour standing at room temperature.

The invention claimed is:

1. A process for preparing a stable emulsion/dispersion of an oil and an aqueous phase comprising adding
a β-glucans rich powder of granulate containing at least 12% by weight of β-glucans having a molecular weight of more than 1,000,000 Daltons in a step-wise sequence to the oil phase; mixing and dispersing the β-glucan in the oil phase and then adding the aqueous phase at temperatures below 40° C. with concomitant mixing and stirring to form an oil-in-water emulsion or a water-in-oil emulsion.

2. A process according to claim 1, wherein the aqueous phase is warmed to at least 25° C. prior to addition.

3. A process according to claim 1, wherein the aqueous phase is warmed to at least 30° C. prior to addition.

4. A process according to claim 1, wherein the aqueous phase is added at room temperature.

5. A process according to claim 1, wherein mixing and stirring takes place using a low-or non-shear mixing.

6. A process according to claim 1, wherein the β-glucans rich substrate contains at least 13% by weight of β-glucans on a dry weight basis.

7. A stable emulsion/dispersion of an oil and an aqueous phase produced according to the process in claim 1, wherein the β-glucans rich substrate, is the active emulsifying component.

8. A stable emulsion/dispersion of an oil and an aqueous phase produced according to the process in claim 1, wherein the β-glucans rich substrate, is derived from oat or barley grain.

9. A stable emulsion/dispersion of an oil and an aqueous phase produced according to the process in claim 1, wherein the β-glucans rich powder or granulate is contained in a oil phase or to a part of the oil phase.

10. A stable emulsion/dispersion of an oil and an aqueous phase produced according to the process in claim 1, wherein the β-glucans are (1-3), (1-4)-β-D-glucans from oat and barley grains.

11. A stable emulsion/dispersion of an oil and an aqueous phase produced according to the process in claim 1, wherein the β-glucans rich substrate is utilized in the form of granulates, particulate solid state, or in powder form.

12. A stable emulsion/dispersion of an oil and an aqueous phase produced according to the process in claim 1, wherein the β-glucans rich substrate contains at least 12 by weight of β-glucans on a dry weight basis.

13. A stable emulsion/dispersion of an oil and an aqueous phase produced according to the process in claim 1, wherein the molecular weight of the β-glucans in the β-glucans rich substrate is at least 1,000,000 Daltons.

14. A stable emulsion/dispersion of an oil and an aqueous phase produced according to the process in claim 1, wherein the β-glucans rich substrate is added at a level of between 2% and 10%, of the final mixture formulation.

15. A stable emulsion/dispersion of an oil and an aqueous phase produced according to the process in claim 1, wherein the oil component within the product emulsion/dispersion ranges from 10% to 80%, the rest being the aqueous component.

16. A stable emulsion/dispersion of an oil and an aqueous phase produced according to the process in claim 1, wherein the oil phase can be any edible vegetable oil or vegetable fat in the melted state of the group comprising; olive oils, rapeseed oil, sunflower oil, soya oil, maize oil, cotton-seed oil, peanut oil, sesame oil, shea nut fats, cereal germ oil such as wheat germ oil, grape kernel oil, palm oil and palm kernel oil, coconut fats, or any animal fat or fat rich material such as butter or butterfat or fish oils, or any blends and combinations of these materials.

17. A stable emulsion/dispersion of an oil and an aqueous phase produced according to the process in claim 1, for use as a suitable base in a full-fat or reduced-fat preparation.

18. A stable emulsion/dispersion of an oil and an aqueous phase produced according to the process in claim 1, for use as a full-fat or reduced-fat ingredient in a foodstuff.

19. A stable emulsion/dispersion of an oil and an aqueous phase produced according to the process in claim 1, for use as a base in a full-fat or reduced-fat ingredient in a mayonnaise.

20. A stable emulsion/dispersion of an oil and an aqueous phase produced according to the process in claim 1, for use as a base in a full-fat or reduced-fat ingredient in a dressing.

21. A stable emulsion/dispersion of an oil and an aqueous phase produced according to the process in claim 1, for use as a base in a full-fat or reduced-fat ingredient in a dip.

22. A stable emulsion/dispersion of an oil and an aqueous phase produced according to the process in claim 1, for use as a base in a reduced-fat spread based on mixtures of butters, other edible fats and water or any suitable combination of fats, oils and water.

23. A stable emulsion/dispersion of an oil and an aqueous phase produced according to the process in claim 1, for use as a full-fat or reduced-fat ingredient in a reduced or normal fat sauce.

24. A stable emulsion/dispersion of an oil and an aqueous phase produced according to the process in claim 1, for use as a full-fat or reduced-fat ingredient in a baked product.

25. A stable emulsion/dispersion of an oil and an aqueous phase produced according to the process in claim 1, for use as a full-fat or reduced-fat ingredient in a cosmetic product for atopic application.

26. A stable emulsion/dispersion of an oil and an aqueous phase produced according to the process in claim 1, in the form of a water-in-oil emulsion.

27. A stable emulsion/dispersion of an oil and an aqueous phase produced according to the process in claim 1, in the form of an oil-in-water emulsion.

28. A process according to claim 1, wherein the β-glucans rich substrate contains at least 13% by weight of β-glucans on a dry weight basis.

29. A process according to claim 1, wherein the β-glucans rich substrate contains at least 14% by weight of β-glucans on a dry weight basis.

30. A process according to claim 1, wherein the β-glucans rich substrate contains at least 15% by weight of β-glucans on a dry weight basis.

31. A stable emulsion/dispersion of an oil and an aqueous phase produced according to the process in claim 1, wherein the β-glucans rich substrate contains at least 13% by weight of β-glucans on a dry weight basis.

32. A stable emulsion/dispersion of an oil and an aqueous phase produced according to the process in claim 1, wherein the β-glucans rich substrate contains at least 14% by weight of β-glucans on a dry weight basis.

33. A stable emulsion/dispersion of an oil and an aqueous phase produced according to the process in claim 1, wherein the β-glucans rich substrate contains at least 15% by weight of β-glucans on a dry weight basis.

34. A stable emulsion/dispersion of an oil and an aqueous phase produced according to the process in claim 1, wherein the molecular weight of the β-glucans in the β-glucans rich substrate is at least 1.5 million Daltons.

35. A stable emulsion/dispersion of an oil and an aqueous phase produced according to the process in claim 1, wherein the β-glucans rich substrate is added at a level of up to 25%, of the final mixture formulation.

* * * * *